(12) United States Patent
Korotkov

(10) Patent No.: US 7,869,636 B2
(45) Date of Patent: Jan. 11, 2011

(54) METHOD FOR DETERMINING THE ANXIETY LEVEL OF A HUMAN BEING

(76) Inventor: Konstantin Georgievich Korotkov, RU. 191040, St. Petersburg, Kuznechny per.. d.14B, kv.6 (RU)

( * ) Notice: Subject to any disclaimer, the term of this patent is extended or adjusted under 35 U.S.C. 154(b) by 1491 days.

(21) Appl. No.: 10/547,138

(22) PCT Filed: Feb. 25, 2003

(86) PCT No.: PCT/RU03/00074
§ 371 (c)(1),
(2), (4) Date: Aug. 24, 2005

(87) PCT Pub. No.: WO2004/075752
PCT Pub. Date: Sep. 10, 2004

(65) Prior Publication Data
US 2006/0084845 A1    Apr. 20, 2006

(51) Int. Cl.
*G06K 9/00* (2006.01)
(52) U.S. Cl. ...................... 382/128; 382/100
(58) Field of Classification Search ............. 382/100, 382/128
See application file for complete search history.

(56) References Cited
U.S. PATENT DOCUMENTS

| | | | | |
|---|---|---|---|---|
| 3,163,557 A | * | 12/1964 | Brutten et al. | 118/701 |
| 3,241,431 A | * | 3/1966 | Brutten et al. | 356/71 |
| 4,195,641 A | * | 4/1980 | Joines et al. | 600/346 |
| 5,349,168 A | * | 9/1994 | Wilen | 219/730 |
| 6,676,611 B1 | * | 1/2004 | Bromba | 600/587 |
| 6,952,490 B2 | * | 10/2005 | Lee | 382/124 |
| 2003/0023145 A1 | * | 1/2003 | Lee et al. | 600/300 |

FOREIGN PATENT DOCUMENTS

SU    1715316 A1 *    2/1992

OTHER PUBLICATIONS

"Aura and Consciousness: New Stage of Scientific Understanding", K. Korotkov, translated from Russian by author, edited by Roger Taylor, 2nd. Revised edition, 1999, pp. 17-108.*

* cited by examiner

*Primary Examiner*—Wenpeng Chen
(74) *Attorney, Agent, or Firm*—John D. Gugliotta, PE, Esq

(57) ABSTRACT

The invention relates to medicine and can be used for determining the anxiety level of a human being. According to said invention, in order to determine the anxiety level of a human being, the structures of a gas-discharge luminosity are fixed around the studied part of the same area of a human skin through a polymer film and without it, each structure is converted into a digital code, the quantitative parameters of the luminosity structure reflecting two-dimensional geometric characteristics of the gas-discharge luminosity are defined and the totality of the parameters of each structure is presented in the form of a point which is situated in a multidimensional parameter space. The level of anxiety of a human being is determined by the distance between the points for structures produced through the film and without it. The less the distance is, the lower the anxiety level is.

11 Claims, 2 Drawing Sheets

METHOD FOR DETERMINING THE ANXIETY LEVEL OF A HUMAN BEING

TECHNICAL FIELD

This invention relates to medicine and can be used for the determining the anxiety level of a human being.

BACKGROUND OF THE INVENTION

Patent SU, A, 106401 protects a method of determining the human physiological state by way of taking still pictures. In order to fix the structure and details of a subject invisible by the unaided eye in a picture, as well as the deep structure of a subject, the latter is put into high frequency electrical field; a photomaterial is placed between the electrode of high frequency circuit forming a condenser coating and the subject's surface.

This method enables to fix the structure of gas discharge luminosity around a biological subject in photomaterial and estimate its physiological state in the moment of taking the picture. The disadvantage of this method is the fact that it doesn't comprise quantitative characteristics, which gives no opportunity to perform a comparative evaluation of a subject in different points of time and compare the state of various subjects.

Patent SU, A, 935076 protects a method of determining the human functional state by means of recording and comparing the structure of gas discharge luminosity in electrical field around a subject as a whole or its part (fingertips) at initial level (at the absence of vegetovascular crisis) and on the threshold of a crisis.

When this method is realized, quantitative criteria of estimation of state of a biological subject are introduced, which allows performing comparison of this state in different points of time. The disadvantages of this method consist in low accuracy and reliability of determining the human state in view of the fact that only one parameter characterizing the luminosity structure is taken into account, and namely the length of gas discharge streamer. Furthermore, the process of gaining information is quite time and labor-consuming: photographs shall be taken, processed, measured by common measurement device; the results of measurement shall be compared.

The disadvantage of the method is also the fact that the estimation of state of a biological subject is performed only in rather a narrow range of changes of a one-dimensional geometric parameter—streamer length (from 15 to 30% as compared to the initial level). It is absolutely unclear how to assess a subject's state if the changes of this parameter exceed the given limits.

Patent RU, C1, 2141250 protects a method, enabling to determine human physiological state by way of fixing and comparing the structure of gas discharge luminosity around the reference subject and the studied subject in electromagnetic field, converting the fixed structures of gas discharge luminosity around the reference and the studied subjects into a digital code, determining quantitative parameters of these structures, which reflect their two-dimensional geometric characteristics, identifying corresponding points which are situated in a multidimensional space of the mentioned parameters for the reference and the studied subjects, and determining the deviation of energoinformational state of the studied subject from that of the reference subject by the distance between these points; quantitative parameters of the structures of gas discharge luminosity, reflecting their spectral, brightness, and fractal characteristics, can be additionally defined, hence the abovementioned points which are situated in a multidimensional space are identified basing on these parameters, too.

This technical solution is taken as prototype of the present invention.

It provides for accuracy and reliability of assessment of human physiological state on the whole, however does not enable to specify the component of this state related only to the functioning of vegetative system. It is worth mentioning that the state of vegetative nervous system correlates with the level of anxiety (stress), moreover, the determining the this level has practical importance, particularly, when the control of state of dispatchers and operators of technical complexes, control of access in safety systems, etc. is performed.

SUMMARY OF THE INVENTION

An object of the present invention is to determine the anxiety level of a human being.

According to said invention, in order to determine the anxiety level of a human being, the structures of a gas-discharge luminosity are fixed around the studied part of the same area of a human skin through a polymer film and without it, each structure is converted into a digital code, the quantitative parameters of the luminosity structure reflecting two-dimensional geometric characteristics of the gas-discharge luminosity are defined and the totality of the parameters of each structure is presented in the form of a point which is situated in a multidimensional parameter space, the level of anxiety of a human being is determined by the distance between the points for structures produced through the film and without it, at that the less the distance is, the lower the anxiety level is; polyethylene or polypropylene or polyvinylchloride or polystyrene film can be used as a polymer film; the width of polymer film can be from 10 to 600 mcm; quantitative parameters of the structures of luminosity can be additionally determined, reflecting their brightness characteristics and/or spectral characteristics and/or fractal characteristics.

The applicant has not found any sources containing data on technical solutions, identical to the claimed one. That enables to conclude that the invention conforms to the criterion "novelty" (N).

Owing to the fact that the studied area of a human skin is covered by a polymer film, the influence of factors referred to the state of vegetative nervous system (blood microcirculation and perspiration) in the zone of the studied area of a human skin on the level of gas discharge luminosity is excluded; thus, comparing the structure of gas discharge luminosity of the area of skin registered through the polymer film with the structure of gas discharge of the same part, registered without it, the information on the state of vegetative nervous system and the level of anxiety (psychological stress) of a human being can be obtained.

The applicant has not found any information on the influence of distinguishing features of the invention on the achievable technical result. The mentioned condition enables to conclude that the claimed invention conforms to the criterion "inventive step" (IS).

BRIEF DESCRIPTION OF THE DRAWINGS

Hereinafter the invention is illustrated by detailed description of its embodiment with references to drawings as follows.

DESCRIPTION OF THE PREFERRED EMBODIMENT

Figure 1:
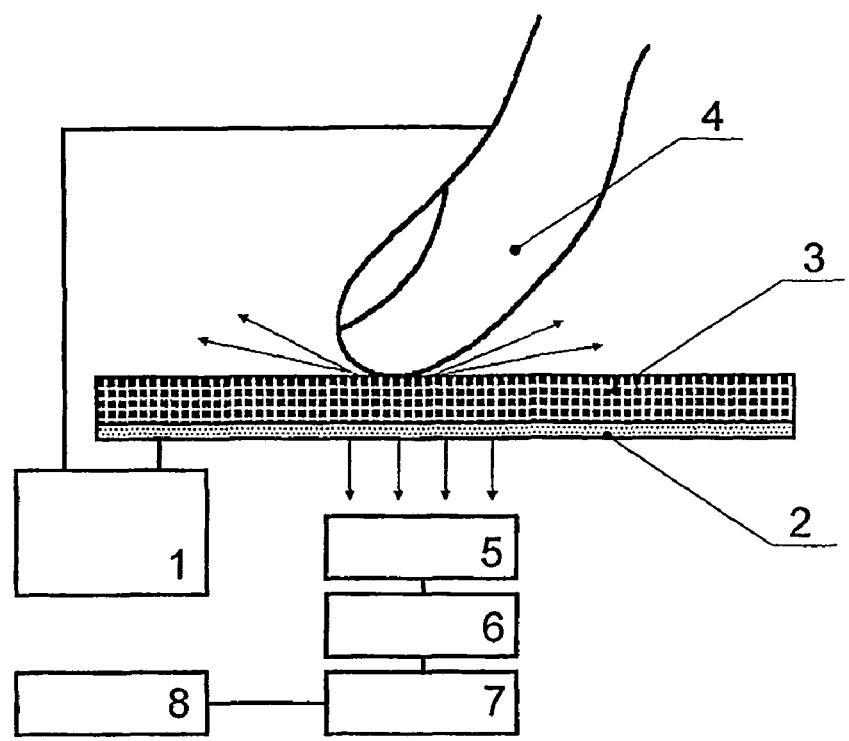
FIG. 1 shows a scheme illustrating obtaining the structure of gas discharge luminosity around the studied area of skin without a polymer film.
Figure 2:
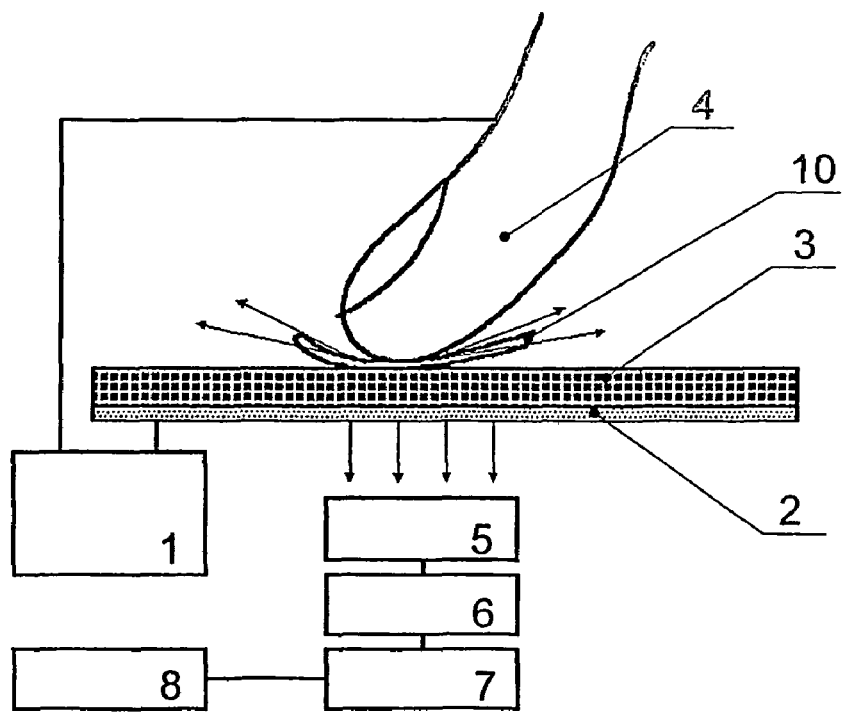
FIG. 2 shows a scheme illustrating obtaining the structure of gas discharge luminosity around the studied area of skin through a polymer film.

The proposed method is embodied as follows.

The electromagnetic field with intensity $10^6$-$10^8$ V/cm is created on the surface of glass plate 3 by means of electronic pulse generator 1 with amplitude 10-20 kV, duration 10 msec, duty ratio 1000 Hz, with pulses fed by pulse strings 0.5 sec long, by electrode 2 performed in the form of a layer of optically transparent material (in the given case—thin layer of $SnO2$ 200 μm thick). In the particular embodiment the electrical pulse generator "Corona" is applied, manufactured by Russian company "Kirlionics Technologies International Ltd." (St. Petersburg).

In the first particular embodiment (a person with high level of anxiety), an area of skin of finger 4 of a person contacts (first directly) with the surface of the glass plate 3 (FIG. 1). The electromagnetic field stimulates gas discharge luminosity around finger 4.

By means of objective lens 5 this luminosity is transferred to optoelectronic digital converter 6, where it is converted into a digital code. In the given case the converter 6 represents a matrix structure made on the basis of a charged coupled device (the so-called CCD-structure). The signal comes from the output of the optoelectronic digital converter 6 to the computer input 7, where quantitative parameters of structure of gas discharge luminosity around finger 4 are determined. In the particular embodiment parameters reflecting two-dimensional geometric characteristics of luminosity structures, as well as brightness characteristics, are determined. Gas discharge luminosity around finger can be represented in the form of two-dimensional color image in computer (7) display 8.

Figure 5:
FIG. 5 shows gas discharge luminosity corresponding to the condition of FIG. 1, typical of a person with low level of anxiety.

Then the totality of quantitative parameters is determined as point 9, shown in FIG. 5, which is situated in a multidimensional parameter space in computer 7. The software described in book by K. Korotkov, Basic of GDV bioelectrography, SPb, 2001, p. 302-335 (Chapter 21: "The description of work of basic software") is used and is attached hereto as an Appendix (along with the English language publication version entitled "Human Energy Field Study with GDV Electrograph", Chapter 19, pages 280-326, published in 2002.

Then the same area of skin of finger 4 contacts with polymer film 10, which is located between finger 4 and glass plate 3, the structure of gas discharge luminosity is registered through film 10, at that.

In the particular embodiment the film is produced from polyethylene and is 80 mcm thick.

Any polymer film can be used; however it is more preferable to use polyethylene, polypropylene, polyvinylchloride or polystyrene. The film may be 10-600 μm thick.

In the particular embodiment axes P1 and P2 correspond to the quantitative parameters of structures of luminosity, reflecting their two-dimensional geometric characteristics, and axis P3 correspond to the quantitative parameters reflecting brightness characteristics of structures of luminosity, axis P4 reflects spectral, and axis P5—fractal characteristics.

In the discussed embodiment the distance $L_1$ between points 9 and 11 gives grounds to conclude that the energy informational state of the studied subject corresponds to his/her high level of anxiety (high stress).

Points 9 and 11 represent the totality of quantitative parameters of structure of gas discharge luminosity around the finger with and without the polymer film, respectively.

Figure 3:
FIG. 3 shows gas discharge luminosity corresponding to the condition of FIG. 1, typical of a person with high level of anxiety (high level of stress)
Figure 4:
FIG. 4 shows gas discharge luminosity corresponding to the condition of FIG. 2, typical of a person with high level of anxiety (high level of stress)
Figure 6:
FIG. 6 shows gas discharge luminosity corresponding to the condition of FIG. 2, typical of a person with low level of anxiety.
Figure 7:
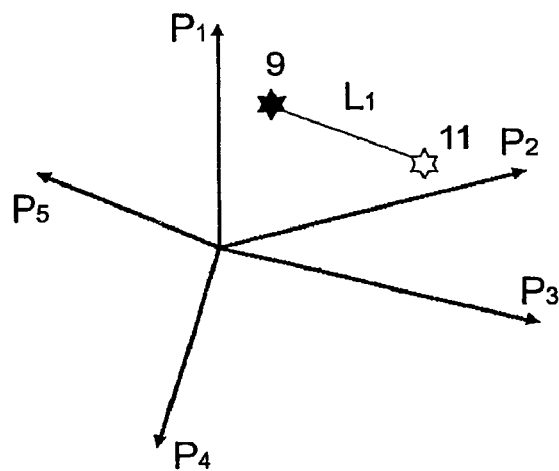
FIG. 7 shows points which are situated in a multidimensional space of quantitative parameters of structures of gas discharge luminosity around the studied area of skin of a person with high level of anxiety.

In the second embodiment the subject of investigation is a person with low level of anxiety. In this case the structures of gas discharge luminosity around the studied area of skin of finger 4, registered without a polymer film and through it, do not differ significantly one from another (FIG. 5 and FIG. 6), while in the first embodiment these structures were visually significantly different (FIG. 3 and FIG. 4).

Figure 8:
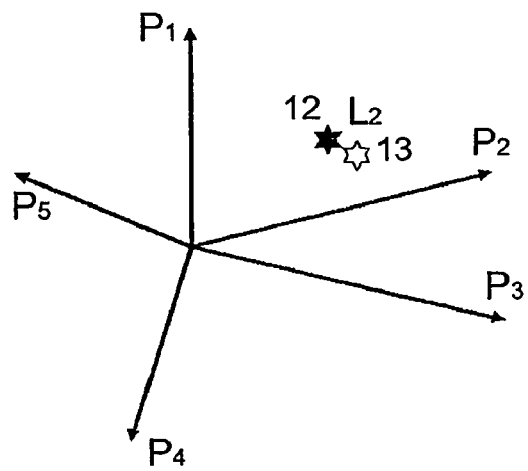
FIG. 8 shows points which are situated in a multidimensional space of quantitative parameters of structures of gas discharge luminosity around the studied area of skin of a person with low level of anxiety.

In the second embodiment point 12 in FIG. 8 corresponds to the structure of gas discharge luminosity registered without polymer film 10, and point 13—to the structure registered through polymer film.

Distance $L_2$ between points 12 and 13 is significantly lower than distance $L_1$ in the first embodiment, which enables to conclude that the energy informational state of the studied subject corresponds to the low level of anxiety.

The observed effect of influence of polymer film on the structure of gas discharge luminosity is stipulated by screening of products secreted by skin during perspiration with respect to the surface of plate 3. Since the level of perspiration relates to the condition of the vegetative nervous system and, respectively, to the level of anxiety and stress, the comparison of gas discharge structures of the studied subject registered directly and through the polymer film allows assessing the energy informational state of the subject from the viewpoint of anxiety.

INDUSTRIAL APPLICABILITY

Common, uncomplicated equipment and known software were applied for the realization of the method, which stipulates that the invention corresponds to the criterion "industrial applicability" (IA).

The invention claimed is:

1. Method of determining an anxiety level of a human being, comprising the steps:
    fixing structures of a gas-discharge luminosity around a studied part of an area of a human skin through a polymer film and without it,
    converting each of the structures into a digital code,
    defining at least one quantitative parameter of the luminosity structure reflecting two-dimensional geometric characteristics of the gas-discharge luminosity,
    measuring totality of said at least one quantitative parameter of each structure presented in the form of a point situated in a multidimensional parameter space, determining the anxiety level of a human being by distance between a point for a structure produced through the film and another point for a structure produced without the film, wherein distance is directly proportional to the anxiety level.

2. Method of claim 1, wherein polyethylene or polypropylene or polyvinylchloride or polystyrene film is used as the polymer film.

3. Method of claim 1, wherein the thickness of the polymer film is from 10 to 600 μm.

4. Method of claim 1, wherein quantitative parameters of structures of luminosity reflecting their brightness characteristics are additionally determined.

5. Method of claim 1, wherein quantitative parameters of structures of luminosity reflecting their spectral characteristics are additionally determined.

6. Method of claim 1, wherein quantitative parameters of structures of luminosity reflecting their fractal characteristics are additionally determined.

7. Method of determining an anxiety level of a human being, comprising the steps:
   a. Fixing structures of a gas-discharge luminosity around a studied part of an area of a human skin through a polymer film and without it,
   b. Converting said fixed structures into a digital code, wherein at least one quantitative parameter of the luminosity structure reflecting two-dimensional geometric characteristics of the gas-discharge luminosity are defined and a totality of said at least one quantitative parameter of each structure presented in the form of a point situated in a multidimensional parameter space,
   c. Correlating said digital code with the level of anxiety of a human being by comparing parameters of a structure of gas discharge luminosity around the studied part of the area of human skin obtained through the polymer film.

8. The method of claim 7, wherein said film is selected from the group comprising: polyethylene; polypropylene; polyvinylchloride; and polystyrene film.

9. The method of claim 8, wherein said polymer film has a thickness from between 10 to 600 μm.

10. Method of determining an anxiety level of a human being, comprising the steps:
    a. Comparing a first structure of gas discharge luminosity of an area of skin registered through a polymer film with a second structure of gas discharge of the same area of the skin registered without the polymer film; and
    b. Correlating quantitative parameters of the first structure with quantitative parameters of the second structure to determine information on a state of vegetative nervous system and a level of anxiety of a human being.

11. The method of claim 10, wherein quantitative parameters of the structures of luminosity are additionally determined, reflecting their brightness characteristics and/or spectral characteristics and/or fractal characteristics.

* * * * *